(12) United States Patent
Kakefuda et al.

(10) Patent No.: US 9,562,867 B2
(45) Date of Patent: Feb. 7, 2017

(54) OPTICAL AXIS ADJUSTMENT DEVICE FOR X-RAY ANALYZER

(71) Applicant: RIGAKU CORPORATION, Akishima-shi (JP)

(72) Inventors: Kouji Kakefuda, Akishima (JP); Ichiro Tobita, Inagi (JP)

(73) Assignee: RIGAKU CORPORATION, Akishima-Shi, Tokyo (JP)

( * ) Notice: Subject to any disclaimer, the term of this patent is extended or adjusted under 35 U.S.C. 154(b) by 191 days.

(21) Appl. No.: 14/533,188

(22) Filed: Nov. 5, 2014

(65) Prior Publication Data
US 2015/0146860 A1  May 28, 2015

(30) Foreign Application Priority Data

Nov. 25, 2013 (JP) .................................. 2013-242713
Sep. 11, 2014 (JP) .................................. 2014-185353

(51) Int. Cl.
*G01N 23/207* (2006.01)

(52) U.S. Cl.
CPC ....... *G01N 23/207* (2013.01); *G01N 2223/314* (2013.01)

(58) Field of Classification Search
CPC G01N 23/20; G01N 23/20016; G01N 23/205; G01N 23/2055; G01N 23/207
See application file for complete search history.

(56) References Cited

U.S. PATENT DOCUMENTS

| 6,947,520 | B2 * | 9/2005 | Yokhin | G01N 23/20 378/207 |
| 7,257,192 | B2 * | 8/2007 | Omote | G01N 23/201 378/70 |
| 2015/0146859 | A1 * | 5/2015 | Kakefuda | G01N 23/207 378/75 |
| 2015/0146860 | A1 * | 5/2015 | Kakefuda | G01N 23/207 378/75 |

FOREIGN PATENT DOCUMENTS

| JP | 1-156643 A | 6/1989 | |
| JP | 1-156644 A | 6/1989 | |
| JP | 1-158952 U | 11/1989 | |
| JP | 3-291554 A | 12/1991 | |
| JP | 04264240 A | * 9/1992 | ........... G01N 23/207 |
| JP | 2007-017216 A | 1/2007 | |

* cited by examiner

*Primary Examiner* — Thomas R Artman
(74) *Attorney, Agent, or Firm* — Buchanan Ingersoll & Rooney PC

(57) ABSTRACT

Provided is an optical axis adjustment device for an X-ray analyzer comprising an incident-side arm, a receiving-side arm, an X-ray source, an incident-side slit, and an X-ray detector, wherein the device comprises a shielding strip disposed at a position blocking X-rays received by the X-ray detector from the X-ray source, and a shielding strip-moving device that rotates the shielding strip around the sample axis relative to the optical axis of X-rays reaching the X-ray detector from the X-ray source to two angle positions, and the amount of deviation in parallelism of the surface of a sample with respect to the optical axis of the X-rays is found on the basis of X-ray intensity values found by the X-ray detector for the two angle positions.

7 Claims, 17 Drawing Sheets

F I G . 8
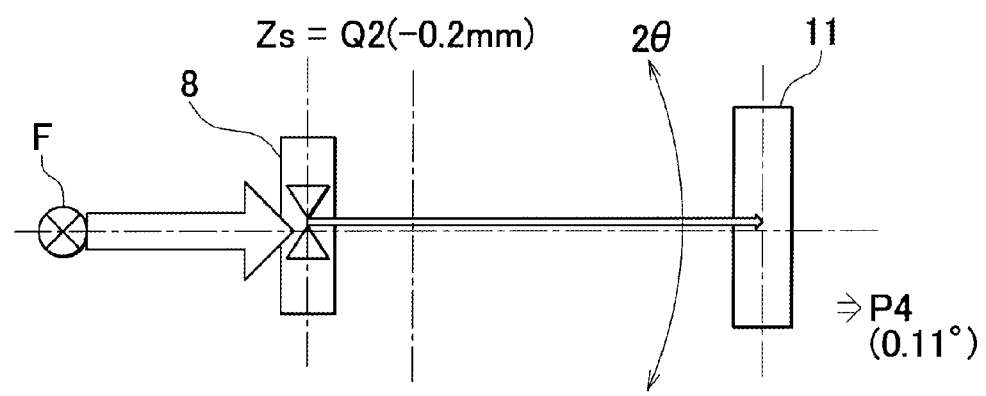

EQUIVALENT TO $\theta$-AXIS ($\beta 2 - \beta 1$) OPENING

OPTICAL AXIS ADJUSTMENT DEVICE FOR X-RAY ANALYZER

BACKGROUND OF THE INVENTION

Field of the Invention

The present invention relates to an X-ray optical axis adjustment device used with an X-ray analyzer that performs measurement by irradiating a sample with X-rays emitted by an X-ray source, and detecting X-rays released by the sample in response to the X-ray irradiation using an X-ray detector.

Description of the Related Art

The X-ray source of the X-ray analyzer is an X-ray focus constituted by a region in which electrons emitted by a cathode such as a filament collide with an anticathode. The X-ray detector is a zero-dimensional X-ray detector not possessing a function of detecting X-ray intensity according to position (i.e., X-ray intensity positional resolution), a one-dimensional X-ray detector capable of positional resolution within a linear region, a two-dimensional X-ray detector capable of positional resolution in a planar region, or the like.

A zero-dimensional X-ray detector is, for example, an X-ray detector using a proportional counter (PC), an X-ray detector using a scintillation counter (SC), or the like. A one-dimensional X-ray detector is, for example, an X-ray detector using a position-sensitive proportional counter (PSPC) or one-dimensional charge-coupled device (CCD) sensor, or an X-ray detector using a plurality of one-dimensionally arrayed photon-counting pixels, or the like. A two-dimensional X-ray detector is, for example, an X-ray detector using a two-dimensional charge-coupled device (CCD) sensor, an X-ray detector using a plurality of two-dimensionally arrayed photon-counting pixels, or the like.

When performing measurement using the X-ray analyzer described above, the centerline of the X-rays reaching the X-ray detector from the X-ray source (i.e., the optical axis of the X-rays) must be set at fixed suitable conditions. The process of setting the optical axis of the X-rays to fixed conditions is generally referred to as adjusting the optical axis.

The optical axis is adjusted by, for example, sequentially performing adjustments such as 2θ-adjustment and θ-adjustment. These various types of adjustment will be described hereafter using a fixed-sample X-ray analyzer as an example.

(I) Fixed-Sample X-Ray Analyzer

First, the fixed-sample X-ray analyzer will be described. In FIG. 15A, a fixed-sample X-ray analyzer 51 comprises an X-ray focus F constituting an X-ray source for emitting X-rays, a sample stage 52 for supporting a sample S in a fixed state, and a zero-dimensional X-ray detector 53 for detecting X-rays given off by the sample S. The X-ray focus F is an X-ray focus for a line focus extending in a direction passing through the surface of FIG. 15A (hereinafter termed the "drawing surface-penetrating direction"). The X-ray focus F may also be a point-focused X-ray focus. An incident-side slit 54 is provided between the X-ray focus F and the sample stage 52. The slit groove of the incident-side slit 54 extends in the drawing surface-penetrating direction in FIG. 15A. The sample stage 52 supports the sample S so that the sample S extends in the drawing surface-penetrating direction.

The X-ray focus F and the incident-side slit 54 are supported by an incident-side arm 55. The incident-side arm 55 rotates around a sample axis X0 extending through the surface of the sample S in the drawing surface-penetrating direction, as shown by arrow θs. This rotational movement may be referred to as θs-rotation, and an operating system for effecting such θs-rotation may be referred to as a θs-axis. θs-rotation is effected using an actuating system comprising a motor of controllable rotational speed, such as a pulse motor, as a power source.

A receiving-side slit 56 is provided between the sample stage 52 and the zero-dimensional X-ray detector 53. The slit groove of the receiving-side slit 56 extends in the drawing surface-penetrating direction in FIG. 15A. The receiving-side slit 56 and the X-ray detector 53 are supported by a receiving-side arm 57. The receiving-side arm 57 rotates around the sample axis X0 independently of the incident-side arm 55, as shown by arrow θd. This rotational movement may be referred to as θd-rotation, and an operating system for effecting such θd-rotation may be referred to as a θd-axis. θd-rotation is effected using an actuating system comprising a motor of controllable rotational speed, such as a pulse motor, as a motive power source.

When using the X-ray analyzer 51 to perform X-ray diffractional measurement upon, for example, a powder sample S, the X-ray focus F and the incident-side slit 54 are θs rotated by the incident-side arm 55 continuously or stepwise at a predetermined angular velocity, while, simultaneously, the receiving-side slit 56 and the X-ray detector 53 are θd rotated by the receiving-side arm 57 continuously or stepwise at the same angular velocity in the opposite direction, as shown in FIG. 15B.

The angle formed by a centerline R1 of X-rays incident upon the sample S from the θs-rotating X-ray focus F with respect to the surface of the sample S is represented by "θ". In other words, the angle of incidence of the X-rays incident upon the sample S is represented by "θ". The centerline of the X-rays is labeled R1, but, in the following description, the X-rays incident upon the sample S may be referred to as incident X-rays R1. The θs-rotation of the X-ray focus F may be referred to as "θ rotation."

When the X-rays incident upon the sample S meets certain diffraction conditions with respect to the crystal lattice plane of the sample S, the X-rays are diffracted by the sample S (i.e., diffracted X-rays is given off by the sample S). The angle formed by the centerline R2 of the diffracted X-rays with respect to the surface of the sample S is always equal to the X-ray angle of incidence θ. Accordingly, the angle formed by the diffracted X-rays with respect to the incident X-rays R1 is twice the X-ray angle of incidence θ. The angle formed by the diffracted X-rays R2 with respect to the incident X-rays R1 is represented by "2θ".

Meanwhile, the θd-rotation of the X-ray detector 53 is performed at the same angular velocity as the θs-rotation of the X-ray source F, with the result that diffracted X-rays R2 emitted from the sample S at angle θ are received by the zero-dimensional X-ray detector 53, which forms angle θ with respect to the surface of the sample S. The X-ray detector 53 forms angle θ with respect to the surface of the sample S, but always forms an angle equal to twice θ with respect to the incident X-rays R1. For this reason, the θd-rotation of the X-ray detector 53 may be referred to as "2θ-rotation."

(II) 2θ-Adjustment

Next, 2θ-adjustment will be described. 2θ-adjustment refers to adjustment performed so as to correctly align the angle 2θ=0° detected by the X-ray detector 53 and the centerline of the X-rays from the X-ray source F reaching the X-ray detector 53. When performing such adjustment, the incident-side arm 55 is first set at an angular position of θs=0°, and the receiving-side arm 57 at an angular position of θd=0°, as shown in FIG. 15A. That is, the X-ray detector 53 is set at an angular position of 2θ=0°.

Next, the sample S is removed from the sample stage 52 to allow X-rays to pass freely through the position of the sample, a incident-side slit 54 of roughly 0.1 mm is set, a receiving-side slit 56 of roughly 0.15 mm is set, the X-ray detector 53 and the receiving-side slit 56 are positioned at 2θ=0°, the X-ray detector 53 and the receiving-side slit 56 are intermittently θd rotated at, for example, steps of 0.002°, and diffracted X-rays are detected by the X-ray detector 53 at each step position. A diffracted X-ray peak waveform such as that shown in FIG. 16A is thus found.

If the amount of deviation of the 2θ-angular position of the center P0 of the full width at half maximum intensity (i.e., FWHM) D0 of the peak waveform with respect to the angular position 2θ=0° of the X-ray detector 53 is within a predetermined tolerance, such as (2/1,000)°, 2θ-adjustment is considered to have been accurately performed. On the other hand, if the amount of deviation of the 2θ-angular position of the center P0 of the full width at half maximum intensity D0 with respect to the 2θ=0° of the X-ray detector 53 is outside of tolerance, the position, for example, of the receiving-side arm 57 in FIG. 15A is adjusted to adjust the position of the X-ray detector 53 and the position of the receiving-side slit 56, after which 2θ-adjustment is again performed.

2θ-adjustment can also be performed by correcting data obtained as the result of actual X-ray diffraction measurement according to the amount of deviation calculated, rather than by moving the position of the X-ray focus F or the X-ray detector 53.

(III) θ-Adjustment

Next, θ-adjustment will be described. In FIG. 15A, θ-adjustment involves adjusting so that the surface of the sample S is parallel to the X-rays R1 incident upon the sample S from the X-ray focus F. When performing such adjustment, the incident-side arm 55 is first set at an angular position of θs=0°, and the receiving-side arm 57 at an angular position of θd=0° in FIG. 15A. That is, the X-ray detector 53 is set at an angular position of 2θ=0°.

Next, an optical axis adjustment jig 58 such as that shown in FIG. 16B is attached to the sample stage 52 instead of the sample S shown in FIG. 15A. In this case, reference surfaces 59a, 59b on the two shoulders of the optical axis adjustment jig 58 facing the optical axis R0 shown in FIG. 15A. Next, the θs-axis and θd-axis are simultaneously rotatingly oscillated the same number of degrees within small angular ranges in opposite directions around the sample axis X0 near θ=0° (i.e., X-rays reaching the zero-dimensional X-ray detector 53 from the X-ray source F are kept in a straight line as the X-rays are rotatingly oscillated around the sample axis X0) to find the angular positions where X-ray detector 53 output is maximum. The angular position of the X-ray focus F and the X-ray detector 53 is then determined to be the position at which θ=0° can be attained.

Techniques for performing conventional X-rays adjustment as described above are disclosed, for example, in patent document 1 (Japanese Patent Laid-Open Publication H01-156644), patent document 2 (Japanese Patent Laid-Open Publication H01-156643), patent document 3 (Japanese Utility Model Laid-Open Publication H01-158952), patent document 4 (Japanese Patent Laid-Open Publication H03-291554), and patent document 5 (Japanese Patent Laid-Open Publication 2007-017216).

In a conventional X-ray analyzer, as described above, an optical axis adjustment jig comprising reference surfaces on two shoulders thereof is used when performing θ-adjustment, and changes in X-ray intensity magnitude are measured while the zero-dimensional X-ray detector is continuously rotated. Such a conventional analyzer apparatus presents the problem that an extremely long time is required to perform measurement.

SUMMARY OF THE INVENTION

The present invention was conceived in view of the problems in the conventional analyzer apparatus described above, it being an object thereof to allow a process of adjusting the optical axis of an X-ray analyzer to be performed in an extremely short period of time.

The X-ray analyzer optical axis adjustment device according to the present invention is an optical axis adjustment device for an X-ray analyzer comprising an incident-side arm that rotates around a sample axis passing through a sample position constituting a position at which a sample is placed, a receiving-side arm that rotates around the sample axis and extends toward a side opposite the incident-side arm, an X-ray source provided on the incident-side arm, an incident-side slit provided on the incident-side arm between the sample position and the X-ray source, an X-ray detector provided on the receiving-side arm, a shielding strip disposed at a position blocking X-rays received by the X-ray detector from the X-ray source, and shielding strip-moving means for rotating the shielding strip around the sample axis relative to an optical axis of the X-rays reaching the X-ray detector from the X-ray source to two different angle positions; wherein an amount of deviation in parallelism of the surface of the sample with respect to the optical axis of the X-rays is found on the basis of X-ray intensity values found by the X-ray detector for each of the two angle positions.

In the arrangement described above, the shielding strip-moving means can be realized via an arrangement that simultaneously rotates the incident-side arm and the receiving-side arm an identical number of degrees in opposite directions around the sample axis with the shielding strip fixed in place. An arrangement in which the shielding strip itself is rotated around the sample axis is also possible. Any other structure in which the optical axis of the X-rays and the shielding strip can be relatively rotated can also be adopted.

In the arrangement described above, the amount of deviation in parallelism of the surface of the sample with respect to the optical axis of the X-rays can be found on the basis of the X-ray intensity values for each of the two angle positions of the shielding strip using an electronic calculating device, such as a computer provided with a CPU and memory.

In the X-ray analyzer optical axis adjustment device according to the present invention, it is preferable that the shielding strip extend only in the receiving direction from the sample axis, as shown by the reference symbol L1 in FIG. 11. This is because, if the shielding strip extends not only halfway but also to the incident side from the sample axis, one side is completely shielded by the shielding strip on the incident side, making it impossible to obtain X-ray intensities for both angle positions of the shielding strip.

In the X-ray analyzer optical axis adjustment device according to the present invention, an X-ray-incident side of the shielding strip may be aligned with the sample axis. This allows accurate intensity data to be obtained for the two angle positions of the shielding strip.

In the X-ray analyzer optical axis adjustment device according to the present invention, the two angles for the shielding strip may be set to a positive-side angle and a negative-side angle so as to cancel out information for the thickness of the shielding strip and obtain only angle information for the shielding strip. Canceling out thickness information in this way allows calculation to be simplified.

In the X-ray analyzer optical axis adjustment device according to the present invention, it is desirable that the length of the shielding strip in a direction along the sample axis be greater than the width of the incident X-ray beam along the sample axis.

In the X-ray analyzer optical axis adjustment device according to the present invention, the X-ray detector is a one-dimensional X-ray detector possessing X-ray intensity positional resolution, i.e., the ability to detect X-ray intensity in predetermined regions on a straight line, and the straight line along which the positional resolution is applied can extend in a direction along the X-ray angle of diffraction.

In accordance with this aspect of the present invention, the need to rotate the X-ray detector when measuring X-ray intensity at two angle positions of the shielding strip with respect to the optical axis of the X-rays is eliminated, allowing the amount of deviation in parallelism of the surface of the sample with respect to the optical axis of the X-rays to be found in an extremely short length of time.

As schematically shown in FIG. 17B, for example, the above-mentioned one-dimensional X-ray detector is an X-ray detector comprising a plurality (such as 256) of pixels 61 of, for example, longitudinal length a=75 μm by lateral length b=10 mm arranged in the direction of the angle of diffraction 2θ. The one-dimensional X-ray detector also includes cases in which a two-dimensional X-ray detector is used as a one-dimensional X-ray detector.

As shown schematically in FIG. 17A, for example, one conceivable two-dimensional X-ray detector comprises pixels 62 of longitudinal length a=100 μm and lateral length b=100 μm arranged two-dimensionally in both the longitudinal and lateral directions. The length La of the two-dimensional X-ray detector in the longitudinal direction is, for example, La=80 mm, and the length Lb in the lateral direction is, for example, Lb=40 mm. In the present invention, a two-dimensional X-ray detector can be used as a one-dimensional X-ray detector by using only that portion of the pixels of the two-dimensional X-ray detector shown in FIG. 17A that corresponds to the pixels having the area shown in FIG. 17B.

Effect of the Invention

In accordance with the X-ray analyzer optical axis adjustment device according to the present invention, out of the different types of optical axis adjustment, θ-adjustment (i.e., finding and correcting the amount of deviation in parallelism of the surface of the sample with respect to the optical axis of the X-rays) is performed only on the basis of diffracted X-ray intensities corresponding to the angle positions of a shielding strip that takes two angle positions, allowing θ-adjustment to be performed extremely quickly. As a result, the overall process of optical axis adjustment, including θ-adjustment, can be performed in an extremely short length of time.

BRIEF DESCRIPTION OF THE DRAWINGS

FIG. 8 is a view showing another step in Zs-axis adjustment;

DESCRIPTION OF THE PREFERRED EMBODIMENTS

Figure 1:
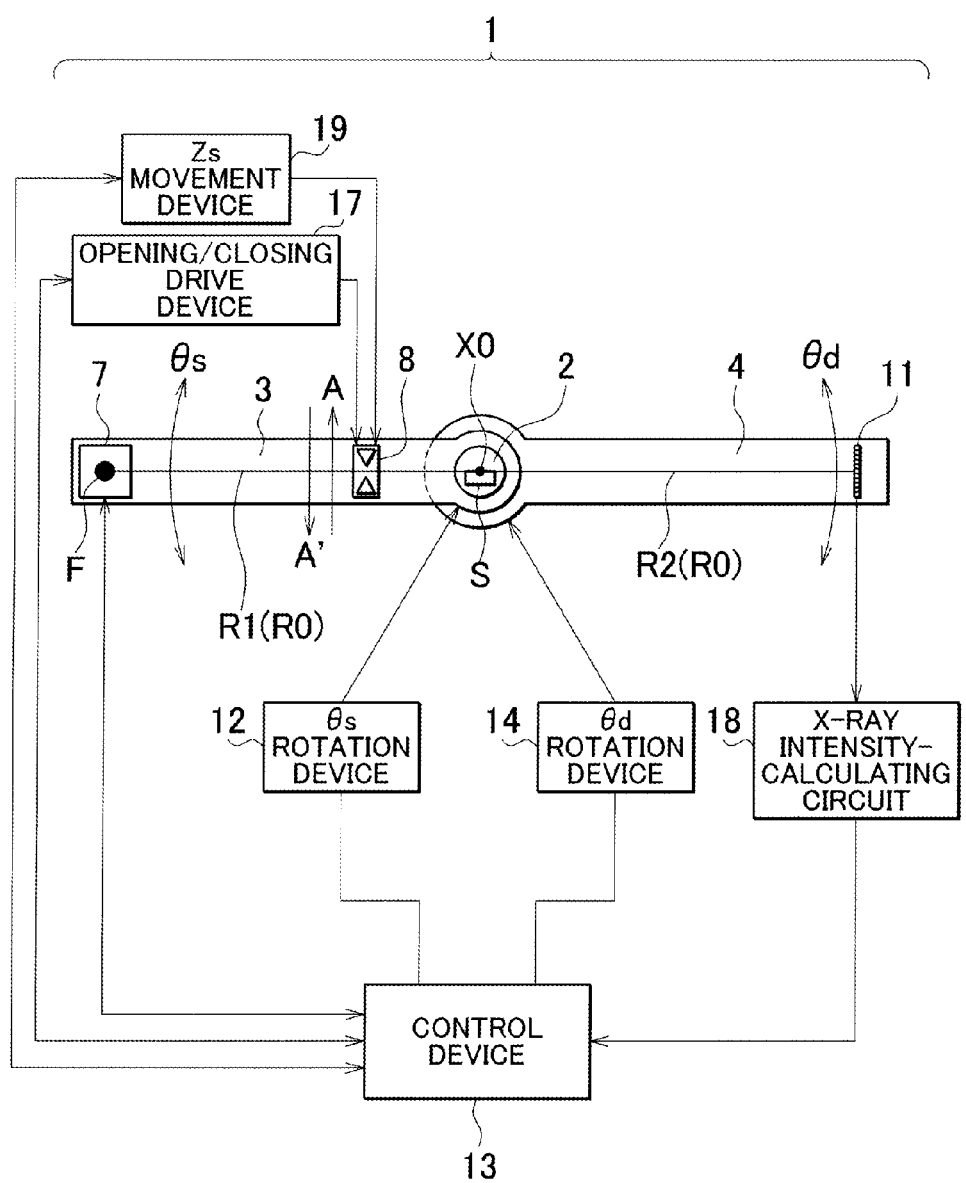
FIG. 1 is a view showing an embodiment of an X-ray analyzer according to the present invention.

An embodiment of the X-ray analyzer according to the present invention will now be described. As shall be apparent, the present invention is not limited to this embodiment. Constituent elements may be shown at other than their actual proportions in the drawings attached to the present specification so as to facilitate comprehension of characteristic portions.

FIG. 1 shows an embodiment of an X-ray analyzer according to the present invention. An X-ray analyzer 1 shown herein comprises a sample stage 2 for supporting a sample S, an incident-side arm 3 capable of rotating around a sample axis X0 constituted by an imaginary line extending through the surface of the sample S in a drawing surface-penetrating direction, and a receiving-side arm 4 capable of rotating around the sample axis X0. The incident-side arm 3 and the receiving-side arm 4 extend in opposite directions. The rotation of the incident-side arm 3 around the sample axis X0 will be referred to as θs-rotation, and the rotation of the receiving-side arm 4 around the sample axis X0 as θd-rotation.

A sample S is in place on the sample stage 2 in FIG. 1, but, when performing an optical axis adjustment operation as described hereafter, the sample S is removed from the sample stage 2 and X-rays allowed to freely pass through the position at which the sample S is placed (hereafter also referred to as the "sample position"), or a center slit or optical axis adjustment jig is placed on the sample stage 2.

The incident-side arm 3 supports an X-ray tube 7 and an incident-side slit 8. An X-ray source F is provided within the X-ray tube 7. A filament (not shown) is provided within the X-ray tube 7 as a cathode, and a target (not shown) as an anticathode. The region in which thermoelectrons released from the filament are capable of colliding with the surface of the target is the X-ray focus, from which X-rays are emitted. The X-ray focus constitutes the X-ray source F. In the present embodiment, the X-ray source F is an X-ray focus for a line focus extending in the drawing surface-penetrating direction. A slit groove of the incident-side slit 8 extends in the drawing surface-penetrating direction.

The receiving-side arm 4 comprises a one-dimensional X-ray detector 11, which is the X-ray detector having X-ray intensity positional resolution within a linear area. The one-dimensional X-ray detector 11 is constituted, for example, by a position-sensitive proportional counter (PSPC), a one-dimensional charge-coupled device (CCD) array, or a one-dimensional photon-counting pixel array. As schematically shown, for example, in FIG. 17B, the one-dimensional X-ray detector 11 is formed by arranging a plurality of pixels (i.e., detection regions) 61 capable of detecting X-rays in a line in a direction orthogonal to the direction in which the receiving-side arm 4 extends. The plurality of pixels 61 are arranged within a region where the one-dimensional X-ray detector 11 can receive X-rays, the region being referred to as an X-ray receiving region. That is, the one-dimensional X-ray detector 11 is capable of detecting X-ray intensity at the pixel level within a linear region orthogonal to the direction in which the receiving-side arm 4 extends. In other words, the one-dimensional X-ray detector 11 possesses positional resolution for X-ray intensity within a linear region orthogonal to the direction in which the receiving-side arm 4 extends.

The incident-side arm 3 is driven by a θs-rotation drive device 12 so as to engage in θs-rotation around the sample axis X0. The θs-rotation drive device 12 rotates the incident-side arm 3 at a predetermined timing and predetermined angular conditions according to commands from a control device 13. The control device 13 is constituted by a computer comprising a central processing unit (CPU) and memory (a storage medium). Software for executing the 2θ-adjustment, Zs-axis adjustment, and θ-adjustment described hereafter is stored in the memory.

The receiving-side arm 4 is driven by a θd-rotation drive device 14 to engage in θd-rotation around the sample axis X0. The θd-rotation drive device 14 rotates the receiving-side arm 4 at a predetermined timing and predetermined angular conditions according to commands from the control device 13. The θs-rotation drive device 12 and θd-rotation drive device 14 are formed by a suitable power transmission mechanism, such as a power transmission mechanism using a worm and a worm wheel.

The slit width of the incident-side slit 8 can be adjusted using a slit opening/closing drive device 17. The slit opening/closing drive device 17 operates according to commands from the control device 13. The incident-side slit 8 is capable of moving in a direction orthogonal to the centerline R0 of the incident X-rays (i.e., vertical direction A-A' in FIG. 1) while maintaining a constant slit width. A Zs-movement device 19 linearly moves the incident-side slit 8 a desired distance from direction A toward direction A' according to commands from the control device 13. The X-ray source F is turned on and off by the control device 13. Output signals from each of the pixels of the one-dimensional X-ray detector 11 are converted by an X-ray intensity-calculating circuit 18 to intensity signals of a predetermined data format and transmitted to the control device 13. In some cases, the X-ray intensity-calculating circuit 18 may be provided within the one-dimensional X-ray detector 11.

Figure 2:
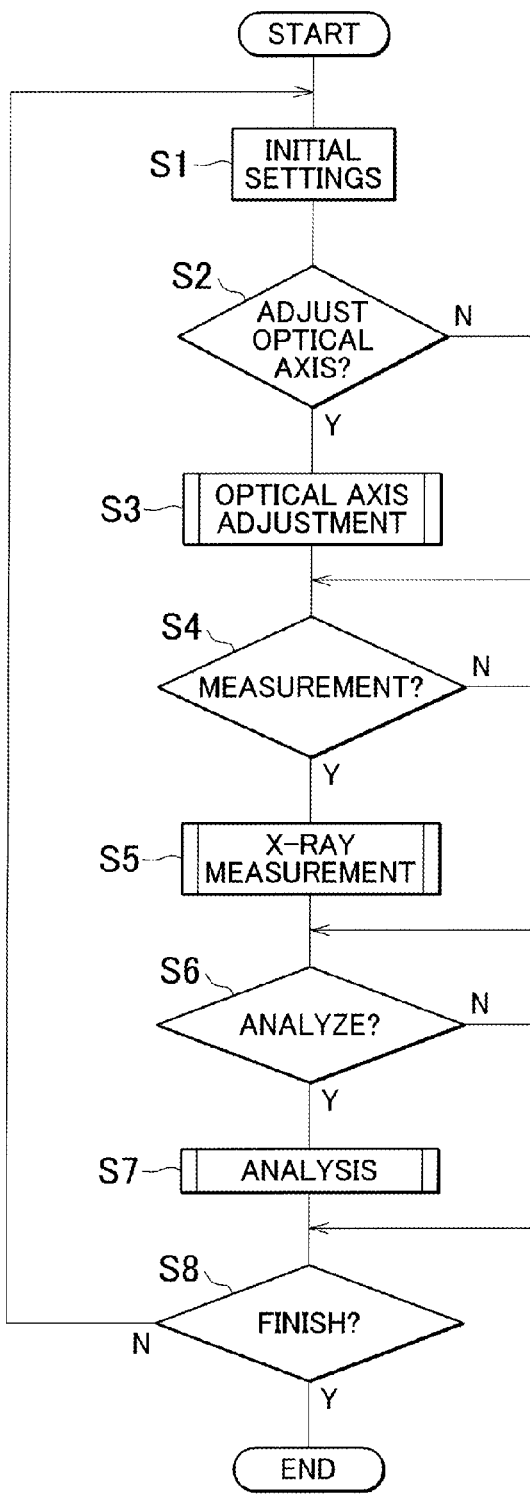
FIG. 2 is a flow chart showing a process executed by the X-ray analyzer shown in FIG. 1.

Upon starting up, the control device 13 sets the various devices shown in FIG. 1 to predetermined initial settings in step S1, as shown in FIG. 2. Next, if instructions to set the optical axis have been inputted using an input device such as a keyboard or a mouse, an assessment of YES is made in step S2, and an optical axis adjustment process is executed in step S3.

If instructions to set the optical axis have not been made in step S2, the process continues to step S4, it is checked whether instructions to perform measurement have been given, and, if so, the process continues to step S5 and X-ray measurement is executed. After X-ray determination is complete, it is checked in step S6 whether instructions to analyze the measured data have been given, and, if so, an analytical process is executed in step S7. Subsequently, it is checked in step S8 whether instructions to finish using the device have been given, and, if so, control is ended.

(1) X-Ray Measurement

Next, an example of the X-ray measurement performed in step S5 of FIG. 2 will be described. In the present embodiment, it will be assumed that X-ray diffractional measurement is being performed upon a powder sample. Various types of X-ray measurement are presently known. As such, the type of X-ray measurement actually executed is selected according to the target X-ray measurement as necessary.

If the X-ray measurement consists of X-ray diffractional measurement being performed upon a powder sample, a powder sample S is placed upon the sample stage 2 in FIG. 1. Specifically, the powder sample S is packed into a predetermined sample holder, which is placed upon the sample stage 2. In this way, the sample S is thus placed at a predetermined sample position within the X-ray analyzer 1, and measurement begins when an operator gives instructions to begin measurement.

Figure 3:
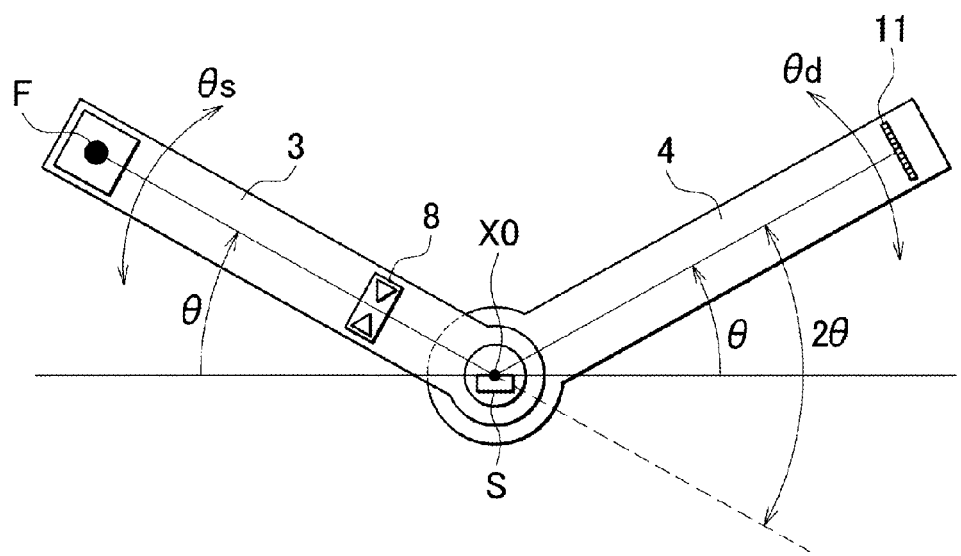
FIG. 3 is a view showing an example of measurement performed by the X-ray analyzer shown in FIG. 1.

Specifically, in FIG. 3, the X-ray source F is θ rotated by the θs-rotation of the incident-side arm 3. Simultaneously, the one-dimensional X-ray detector 11 is 2θ rotated by the θd-rotation of the receiving-side arm 4. While the X-ray source F is undergoing θ-rotation and the X-ray detector 11 is undergoing 2θ-rotation, X-rays emitted by the X-ray source F become incident upon the sample S. When diffraction conditions between the X-rays incident upon the sample S and the crystal lattice plane within the sample S are met, the X-rays are diffracted by the sample S, and the diffracted X-rays are detected by the one-dimensional X-ray detector 11. The X-ray intensity of the diffracted X-rays at the various angle positions for the angle of diffraction 2θ is determined on the basis of the output signals from the X-ray detector 11, and this X-ray intensity becomes X-ray diffractional measurement results data.

The X-ray diffractional measurement described here is one example of X-ray measurement, and another suitable type of measurement other than X-ray diffractional measurement can actually be performed as necessary.

(2) Optical Axis Adjustment

Next, the optical axis adjustment performed in step S3 of FIG. 2 will be described. This optical axis adjustment consists of three types: 2θ-adjustment, Zs-axis adjustment, and θ-adjustment. These various types of adjustment will be individually described hereafter.

(2-1) 2θ-Adjustment

2θ-adjustment is adjustment for aligning the 2θ=0° angle position in the optical system of the X-ray analyzer 1 (FIG. 1) and the centerline of the X-rays reaching the X-ray detector 11 from the X-ray source F.

2θ-adjustment involves determining a θd-correction value for correcting the angle of the X-ray detector 11 with the incident-side slit 8 set to an open state at a predetermined aperture. Specifically, in FIG. 3, the process involves setting the incident-side arm 3 is set to θ=0°, also setting the receiving-side arm 4 to θ=0°, and setting the optical system to the 2θ=0° state shown in FIG. 1, then adjusting so that the centerline R0 of the X-rays reaching the X-ray detector 11 from the X-ray source F aligns with the 2θ=0° angle position of the one-dimensional X-ray detector 11.

In 2θ-adjustment, as shown in FIG. 1, the incident-side arm 3 is first set to θs=0°, the receiving-side arm 4 is set to θd=0°, and the optical system is set to 2θ=0°. Next, the incident-side slit 8 is set to an open state by the opening/closing drive device 17. The sample S is then removed from the sample stage 2, and a center slit 20 is placed on the sample stage 2 in lieu of the sample S, as shown in FIG. 4.

Figure 4:
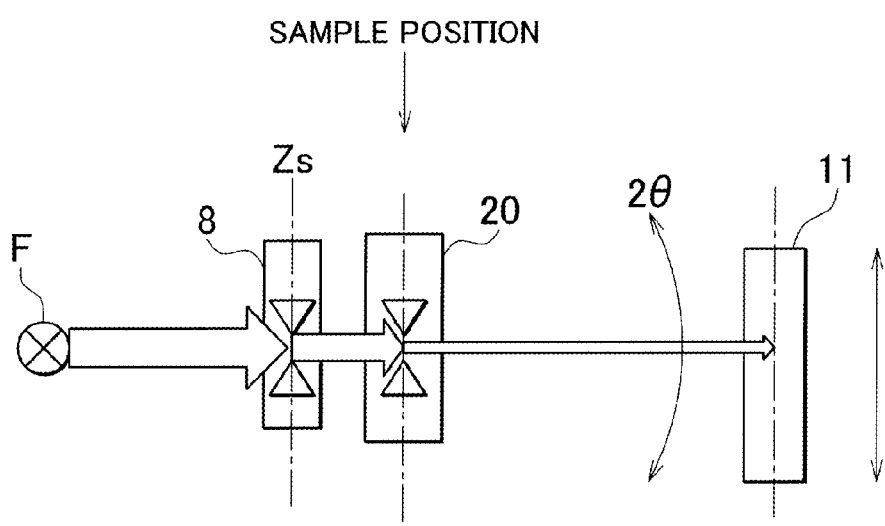
FIG. 4 is a view showing one step in 2θ-adjustment, a type of optical axis adjustment.

With the one-dimensional X-ray detector 11 fixed in the state shown in FIG. 4, X-rays are emitted from the X-ray source F, and X-rays passing through the open incident-side slit 8 and the center slit 20 are detected by the X-ray detector 11. The one-dimensional X-ray detector 11 possesses positional resolution for the x-ray intensity in a direction orthogonal to the direction of the X-rays, thereby the detector 11 can obtain an X-ray profile P1 within a predetermined angular region in the 2θ-direction, as shown in FIG. 5, via one round of X-ray irradiation from the X-ray source F.

Assuming that the peak position of the profile P1 deviates δ0 from 2θ=0°, the amount of deviation δ0 indicates the sum of the amount of deviation of the θd-axis and the amount of deviation of the X-ray detector 11. This being the case, optical axis adjustment for the 2θ-direction can be performed by setting the amount of deviation 50 as the correction value for the θd-axis for the X-ray measurement results data shown in FIG. 5. Specifically, the position of the X-ray detector 11 is adjusted by moving the receiving-side arm 4 a distance of the amount of deviation δ0 in FIG. 3. If the X-ray optical elements, such as slit, monochromator, etc., are mounted on the receiving-side arm 4, the positions of such the X-ray optical elements are also adjusted.

Figure 5:
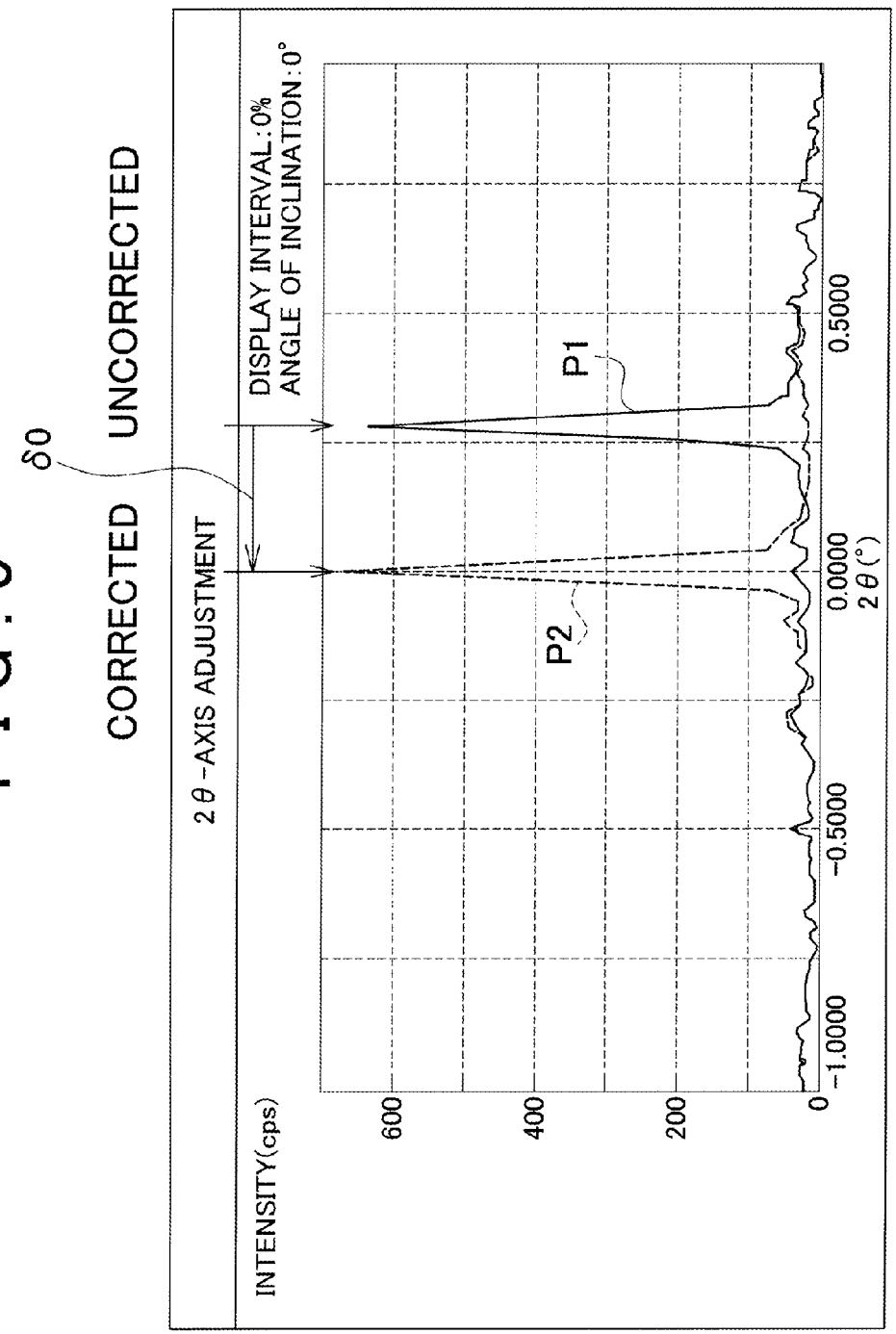
FIG. 5 is a graph showing results from 2θ adjustment.

In the example shown in FIG. 5, δ0 was 0.2831°. It is therefore possible to correct deviation in the 2θ direction, i.e., correct deviation with respect to the θd-axis, by subtracting δ0=0.2831° from the value for 2θ in the data obtained by the X-ray detector 11. Peak waveform P2 shown in FIG. 5 is a corrected peak waveform obtained by correcting the raw measurement data shown by peak waveform P1 by δ0=0.2831° in the negative direction, and the peak of the peak waveform P2 is aligned with 2θ=0°.

(2-2) Zs-Axis Adjustment

Next, Zs-axis adjustment will be described. Zs-axis adjustment involves setting the incident-side slit 8 shown in FIG. 1 to a suitable position with respect to the optical axis R0 of the X-rays reaching the X-ray detector 11 from the X-ray source F. In Zs-axis adjustment, the sample 2 is removed from the sample stage 2 with the X-ray analyzer 1 being in the state shown in FIG. 1 (i.e., 2θ=0°) so that X-rays can freely pass through the sample position.

Figure 6:
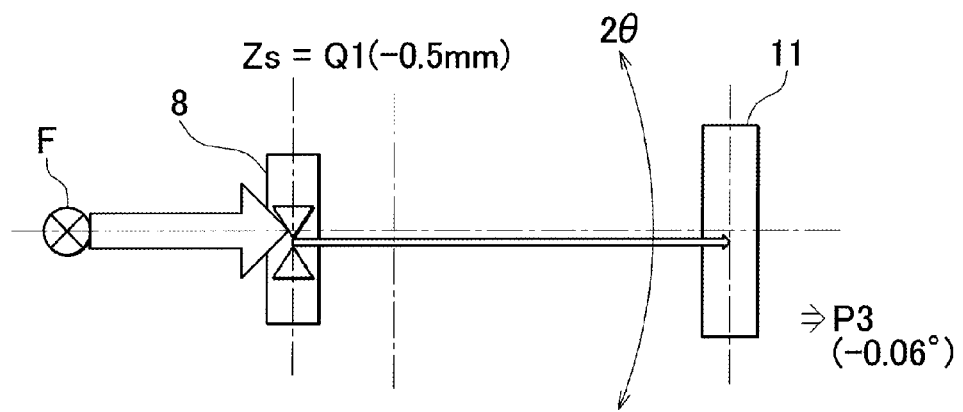
FIG. 6 is a view showing one step in Zs-axis adjustment, another type of optical axis adjustment.

Next, the Zs-axis (i.e., the incident-side slit 8) is moved by the Zs-movement device 19 shown in FIG. 1 to a first position Q1 (such as −0.5 mm) along the A-A' direction shown in FIG. 1, as shown in FIG. 6. X-rays are then emitted by the X-ray source F in this state, and X-rays passing through the incident-side slit 8 are detected by the one-dimensional X-ray detector 11. Because the one-dimensional X-ray detector 11 comprises X-ray-detecting pixels arrayed in the 2θ-direction, the profile P3 shown in FIG. 7 can be obtained through a single round of X-rays irradiation. The peak pp3 of the profile P3 was, for example, 2θ=−0.06°.

Next, the Zs-axis (i.e., the incident-side slit 8) is moved by the Zs-movement device 19 shown in FIG. 1 to a second position Q2 (such as −0.2 mm) along the A-A' direction shown in the FIG. 1, as shown in FIG. 8. X-rays are then emitted by the X-ray source F in this state, and X-rays passing through the incident-side slit 8 are detected by the one-dimensional X-ray detector 11. The profile P4 shown in FIG. 7 can be obtained via this single round of X-ray irradiation. The peak pp4 of the profile P4 was, for example, 2θ=0.11°.

Figure 7:
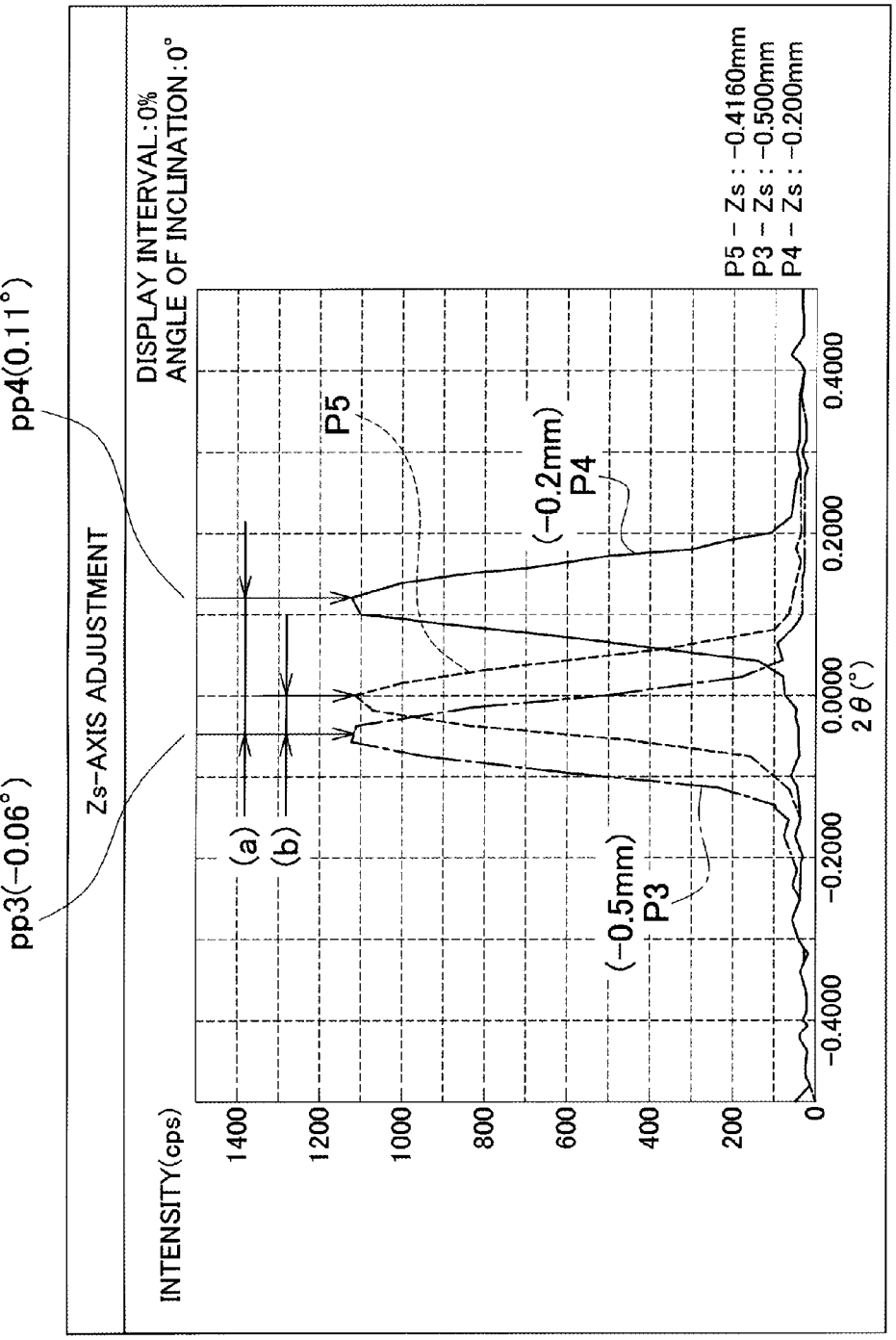
FIG. 7 is a graph showing results from Zs-axis adjustment.

The positional information for Q1 on the Zs-axis shown in FIG. 6 (i.e., −0.5 mm) is projected as pp3 (−0.06°) on the 2θ-axis (i.e., the lateral axis) of the graph shown in FIG. 7. Meanwhile, the position information for Q2 on the Zs-axis shown in FIG. 8 (i.e., −0.2 mm) is projected as pp4 (0.11°) on the 2θ-axis (i.e., the lateral axis) of the graph shown in FIG. 8. In other words, the distance moved by the incident-side slit 8 on the Zs-axis (Q1−Q2=0.5−0.2=0.3 mm) is projected as the distance "pp3-pp4" (=0.06+0.11=0.17°) on 2θ-axis. It is apparent from this that the angle of 0.06° on 2θ-axis is equivalent to the 0.1 mm distance moved by the incident-side slit 8 on the Zs-axis.

Accordingly, it is possible to measure at least two measurement positions Q1, Q2 on the Zs-axis to draw profiles of measurement results on a diffraction-profile graph such as those shown in FIG. 7, find the relationships of the peak positions of the profiles to 2θ=0°, and reflect these relationships in the positions on the Zs-axis in order to accurately find the position on the Zs-axis corresponding to 2θ=0°. In other words, the position on the Zs-axis corresponding to 2θ=0° can be calculated on the basis of the peak position (pp3) in FIG. 7 corresponding to Q1 (FIG. 6) on the Zs-axis and the peak position (pp4) in FIG. 7 corresponding to Q2 (FIG. 8) on the Zs-axis.

For example, assuming that Q1=−0.5 mm, Q2=−0.2 mm, pp3=−0.06°, and pp4=0.11°, the position Zs on the Zs-axis corresponding to the X-ray angle 2θ=0° can be found using the formula $$Zs = -0.5 \text{ mm} + (b/a) \times 0.3 \text{ mm} \quad (1)$$

Wherein $$a = +0.11° - (-0.06°)$$

$$b = 0° - (-0.06°).$$

Using formula (1) above, Zs≈−0.4 mm.

For confirmation, the incident-side slit 8 was replaced at the position Zs=0.4 mm in FIG. 6, and X-rays were detected using the X-ray detector 11. When the measurement results were then plotted on the diffraction line graph shown in FIG. 7, profile P5 was obtained. The peak position of the profile P5 was aligned with 2θ=0°. This showed that the above-mentioned correction formula (1) for the incident-side slit 8 was appropriate.

For further confirmation, the position of the incident-side slit 8 on the Zs-axis was adjusted according to the calculated results, after which X-ray diffractional measurement was performed according to the following three sets of conditions.

(A) An incident-side slit 8 having an divergence angle of (⅔)° was disposed at the position of the incident-side slit 8 in FIG. 6, and X-ray measurement was performed using the one-dimensional X-ray detector 11.

(B) An incident-side slit having a slit width of 0.2 mm was disposed at the position of the incident-side slit 8 in FIG. 6, and X-ray measurement was performed using the one-dimensional X-ray detector 11.

(C) An incident-side slit 8 having a slit width of 0.2 mm was disposed at the position of the incident-side slit 8 in FIG. 6, a center slit was further disposed at the sample position, and X-ray measurement was performed using the one-dimensional X-ray detector 11.

Figure 9:
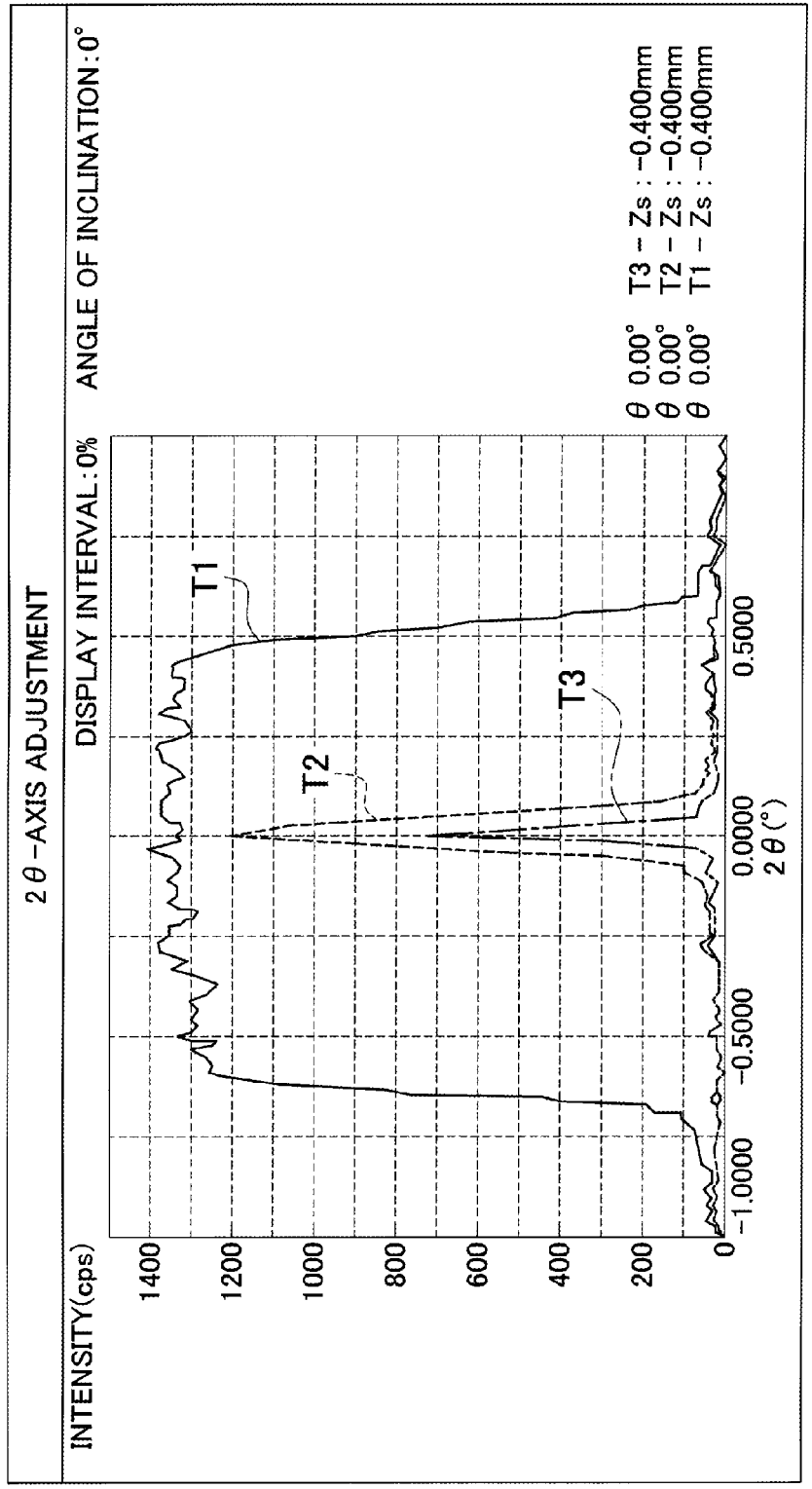
FIG. 9 is a graph showing other results from Zs-axis adjustment.
Figure 10A:
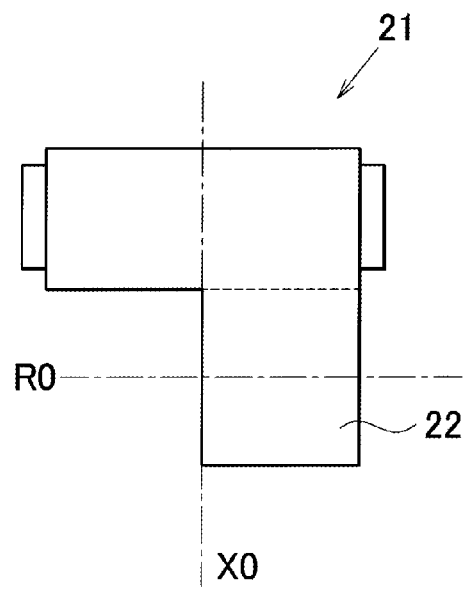
FIG. 10A is a plan view of an example of an optical axis adjustment jig used when performing θ-adjustment, which is yet another type of optical axis adjustment.
Figure 10B:
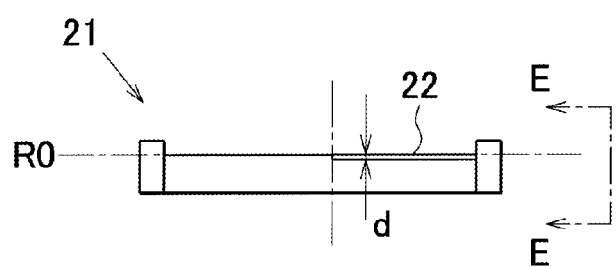
FIG. 10B is a front view of the optical axis adjustment jig.
Figure 10C:
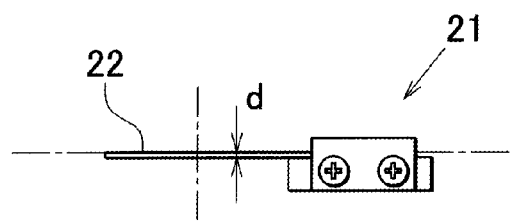
FIG. 10*c* is a side view along line E-E in FIG. 10B.

When the measurement results for the various conditions described above were plotted on the X-ray diffraction diagram shown in FIG. 9, profile T1 was obtained as the measurement results for conditions (A), profile T2 was obtained as the measurement results for conditions (B), an profile T3 was obtained as the measurement results for conditions (C). In all of the results, the peak value appeared at 2θ=0°. It was thus apparent that the position of the incident-side slit 8 on the Zs-axis was correctly aligned to 2θ=0°. It was also apparent that the position was aligned to 2θ=0° regardless of the presence or lack of a center slit.

(2-3) θ-Adjustment

Next, the θ-adjustment variety of optical axis adjustment will be described. The θ-adjustment involves aligning the surface of the sample S in FIG. 1 so as to be parallel to the X-rays R1 incident upon the sample S.

Figure 15A:
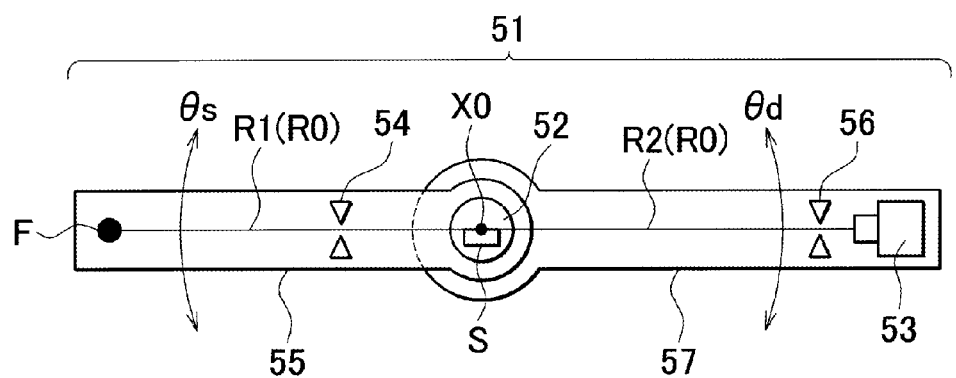
FIG. 15A shows an example of conventional optical axis adjustment.
Figure 15B:
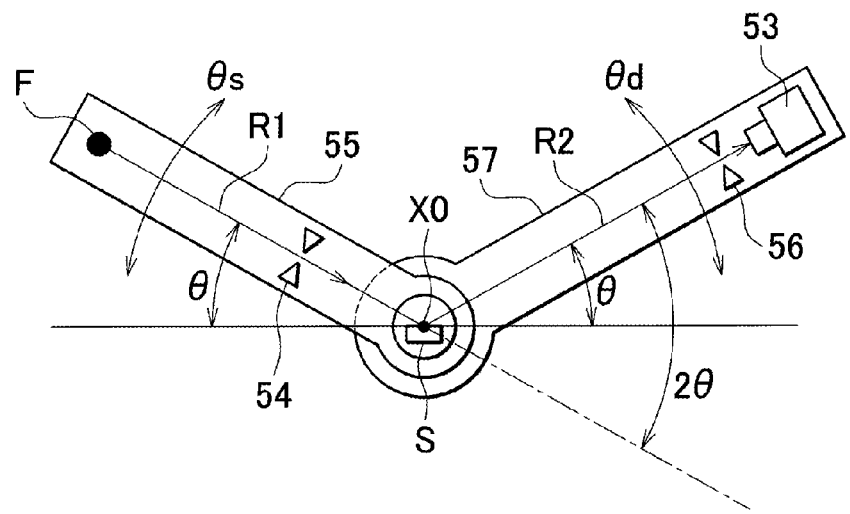
FIG. 15B shows an example of conventional X-ray measurement.
Figure 16A:
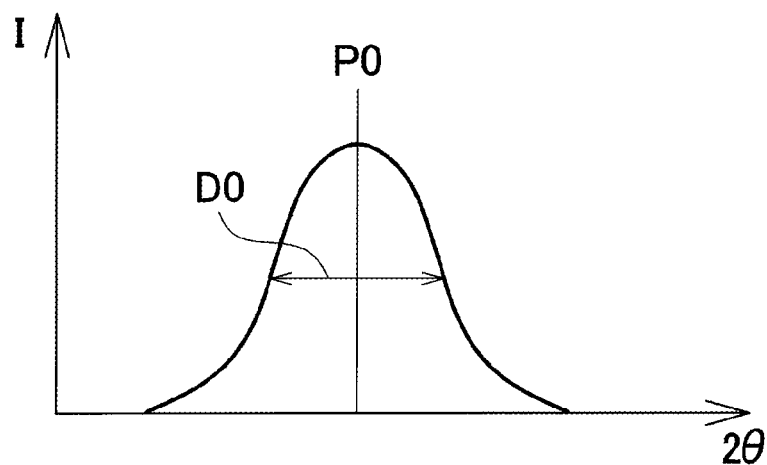
FIG. 16A is a graph showing a diffraction profile obtained using conventional optical axis adjustment.
Figure 16B:
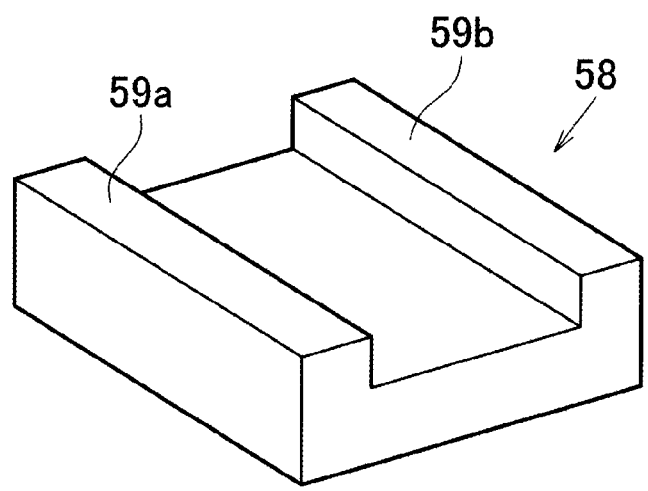
FIG. 16B is a perspective view of an example of an optical axis adjustment jig used in conventional optical axis adjustment.

In a conventional X-ray analyzer, as described using FIGS. 15A and 16B, θ-adjustment is performed by placing the optical axis adjustment jig 58 at the sample position, simultaneously continuously rotating the X-ray source F and the zero-dimensional X-ray detector 53 within a prescribed angle range around the sample position so that the centerline of the X-rays reaching the zero-dimensional X-ray detector 53 from the X-ray source F remained a straight line while measuring the magnitude of the X-ray intensity using the zero-dimensional X-ray detector 53, evaluating the degree of parallelism of the optical axis adjustment jig 58 to the X-ray optical axis on the basis of the X-ray intensity magnitude, and performing e-adjustment on the basis of the evaluation results.

Figure 11:
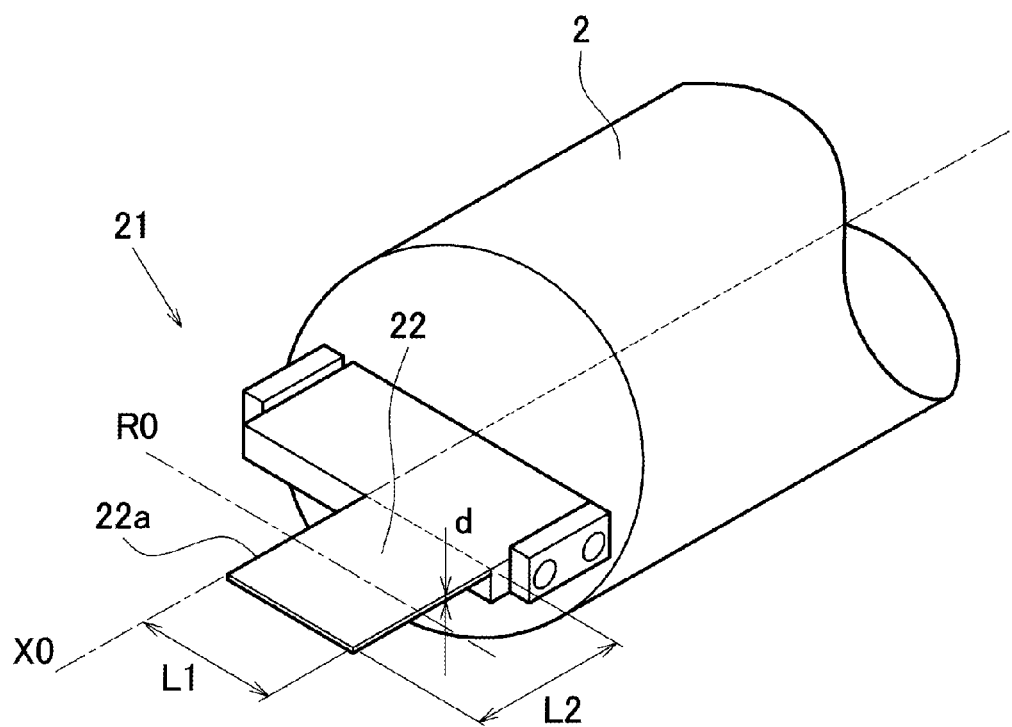
FIG. 11 is a perspective view of an example of the optical axis adjustment jig shown in FIGS. 10A to 10C being attached to an X-ray analyzer.
Figure 12A:
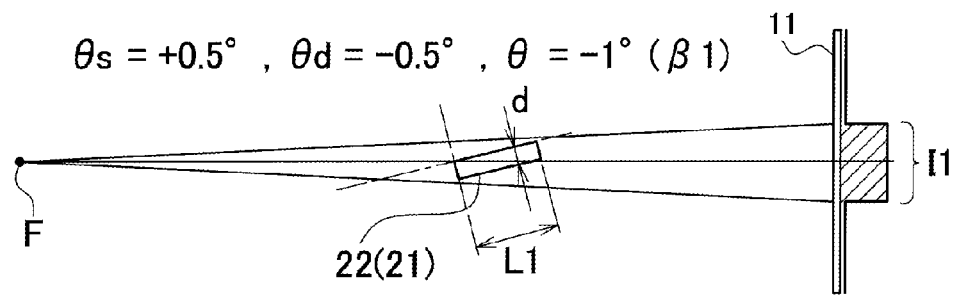
FIGS. 12A, 12B, and 12C are schematic views of three steps performed in succession during θ-adjustment.
Figure 12B:
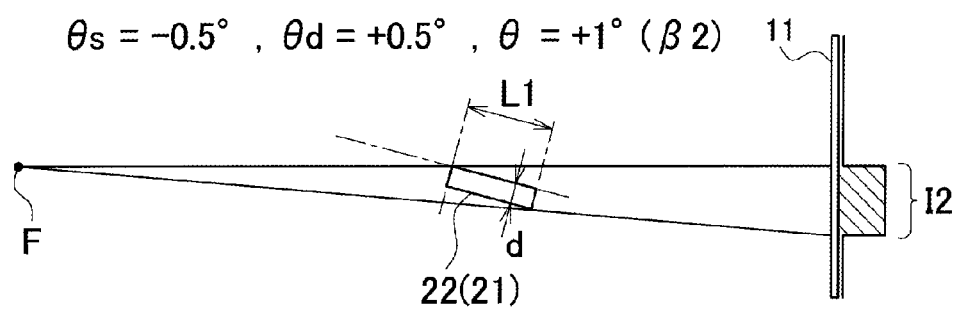
Figure 12C:
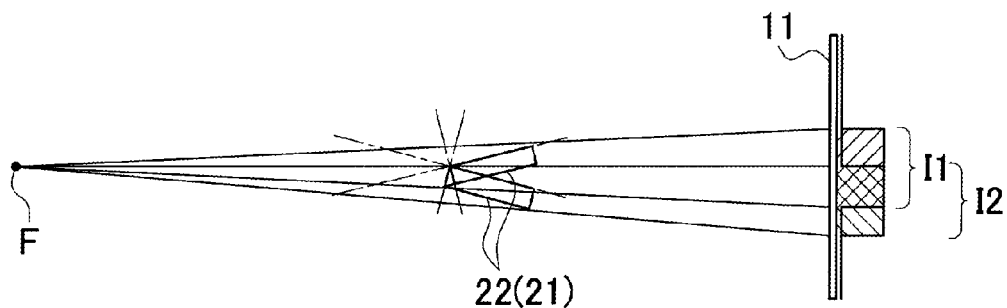

In the present embodiment, by contrast, an optical axis adjustment jig 21 shown in 10A, 10B, and 10C is set in place at a predetermined position on the sample stage 2 instead of the sample S, as shown in FIG. 11, the X-ray source F and the one-dimensional X-ray detector 11 are rotated between two difference positions around the sample position (such as θs=+0.5°, θd=−0.5°, θ−1° (β1) shown in FIG. 12A and θs=−0.5°, θd=+0.5°, θ+1° (β2) shown in FIG. 12B) so that the centerline (i.e., the optical axis) R0 of the X-rays reaching the one-dimensional X-ray detector 11 from the X-ray source F in FIG. 1 remains a straight line (i.e., fixed at 2θ=0°), and the X-ray intensity is measured using the one-dimensional X-ray detector 11 at each position.

The angle described by the X-ray optical axis R0 when the surface of the sample is parallel to the X-ray optical axis R0 is calculated from the relationship between the angle of the X-ray optical axis R0 and the width of the angle of diffraction projected on 2θ. The calculated angle is the e-axis correction value, and the position of the e-axis correction value is aligned with θ=0° of the measurement system.

As shown in FIG. 11, the optical axis adjustment jig 21 comprises a shielding strip 22 for blocking X-rays. An X-ray-incident side 22a of the shielding strip 22 is aligned with the sample axis X0. A roughly central portion of the shielding strip 22 in a direction along the sample axis X0 is aligned with the X-ray optical axis R0. The length L2 of the shielding strip 22 along the sample axis X0 is preferably greater than the width of the incident X-ray beam in a direction along the sample axis X0.

More specifically, the θ-axis is aligned to β1 (for example, −1.0°, as shown in FIG. 12A, and an X-ray intensity I1 is measured using the one-dimensional X-ray detector 11. Next, the θ-axis is moved to β2 (for example, +1.0°), as shown in FIG. 12B, and an X-ray intensity I2 is measured using the one-dimensional X-ray detector 11. Next, the measurement data obtained when the θ-axis is at β1 and at β2 are aligned.

Figure 13A:
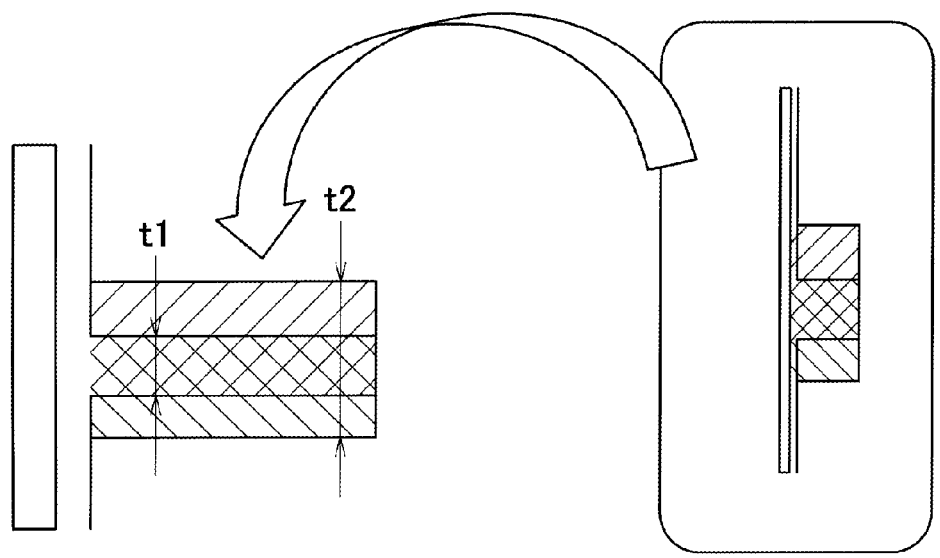
FIGS. 13A and 13B are schematic views of a main process performed during the θ-adjustment according to the present invention.
Figure 13B:
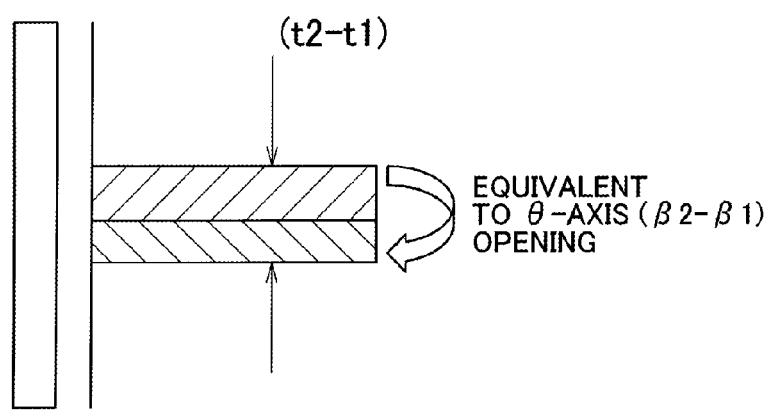

FIG. 13A shows a schematic magnification of measurement data having been aligned as described above. In FIG. 13A, t1 represents the thickness d of the shielding strip 22, and t2 represents the position of the tail of the shielding strip 22. When the value of (t2−t1) in FIG. 13A is found, this value represents the opening level (β2−β1), as shown in FIG. 13B. Accordingly, θ-adjustment can be performed by finding a correction value for the θ-axis so that the value for (t2−t1) is equally spaced around 0.0°.

Figure 14:
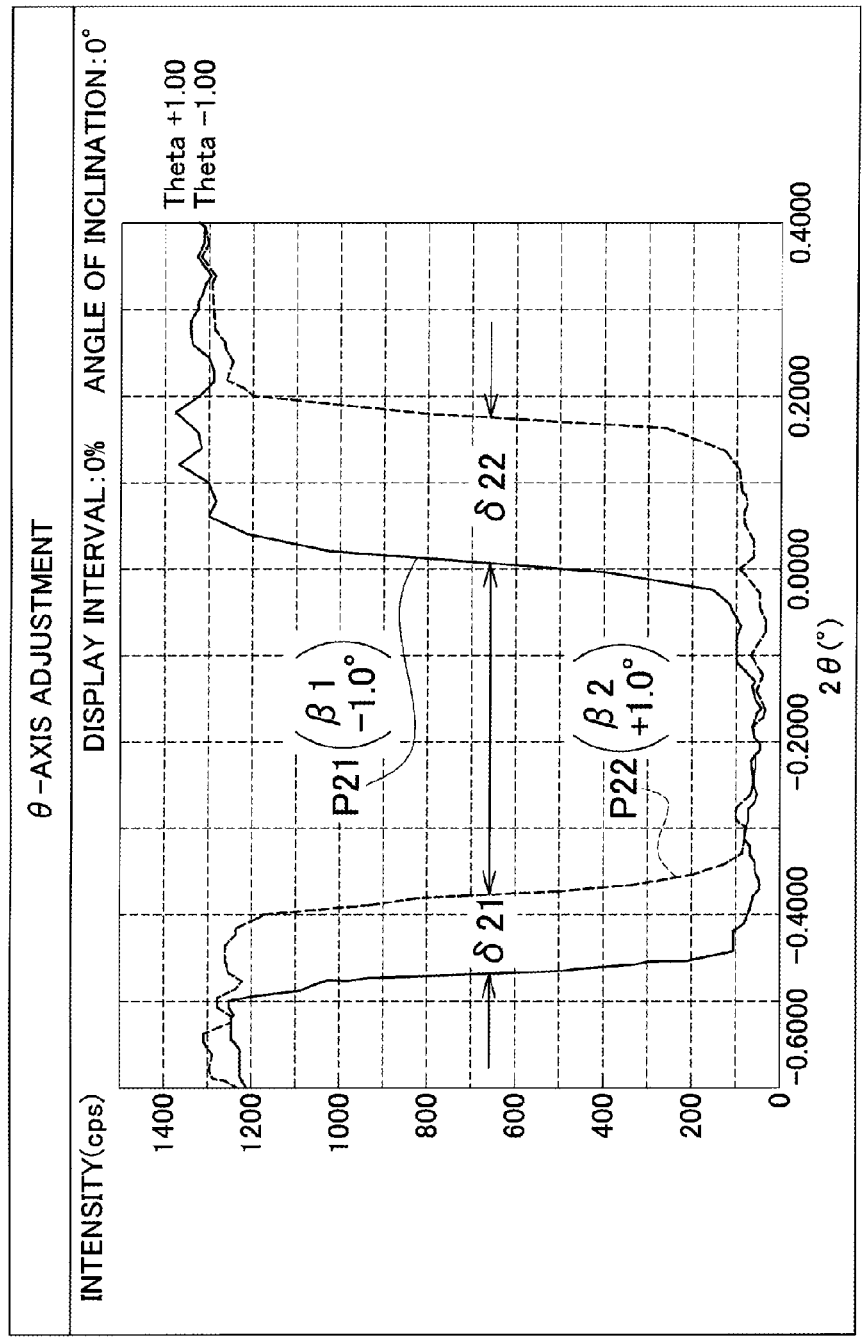
FIG. 14 is a graph for illustrating a main process of the θ-adjustment according to the present invention.

In FIG. 14, P21 is an X-ray profile measured when β1=−1.0° in FIG. 12A. P22 is an X-ray profile measured when β2=+1.0° in FIG. 12B. Here, the difference δ21 between the low angle sides of P21 and P22 is roughly 0.10°. The difference δ22 between the high angle sides of P21 and P22 is roughly 0.17°.

The amount of deviation from the center on 2θ is $$(0.10°+0.17°)\div 2.0-0.10°=0.035° \qquad (2)$$

and the θ-axis correction angle is $$0.035°\times 2.0\div(0.10°+0.17°)\approx 0.259° \qquad (3).$$

Information obtained by shifting the θ-axis ±1.0° is projected on 2θ as (0.10°+0.17°=0.27°). When the θ-axis has been adjusted, δ21 and δ22 have identical values. Because 2° on the θ-axis corresponds to 0.27° on 2θ, formulas (2) and (3) shown above hold true.

Once the three types of adjustment described above 2θ-adjustment, Zs-axis adjustment, and θ-adjustment have been performed, the optical axis adjustment of step S3 in FIG. 2 is complete.

In accordance with the present embodiment, as described above, out of the different types of optical axis adjustment, θ-adjustment (i.e., finding and correcting the amount of deviation in parallelism of the surface of the sample with respect to the optical axis of the X-rays) is performed on the basis only of diffracted X-ray intensities I1 and I2 corresponding to the angle positions of the shielding strip 22, which takes two angle positions β1 (FIG. 12A) and β2 (FIG. 12B), allowing θ-adjustment to be performed extremely quickly. As a result, the overall process of optical axis adjustment, including θ-adjustment, can be performed in an extremely short length of time.

In accordance with the present embodiment, the amount of deviation between the angle of incidence θ of the X-rays with respect to the sample and the θs angle of the incident-side arm 3 and the amount of deviation between the X-ray angle of diffraction 2θ and the θd angle of the receiving-side arm 4 are found by using the capability for X-ray intensity positional resolution possessed by the one-dimensional X-ray detector 11, thereby allowing the process of finding these amounts of deviation and the process of performing optical axis adjustment on the basis of the amounts of deviation to be performed quickly and simply.

Other Embodiments

The foregoing has been a description of a preferred embodiment of the present invention, but the present invention is not limited to this embodiment, and various modifications can be made thereto within the scope of the invention as set forth in the claims.

Figure 17A:
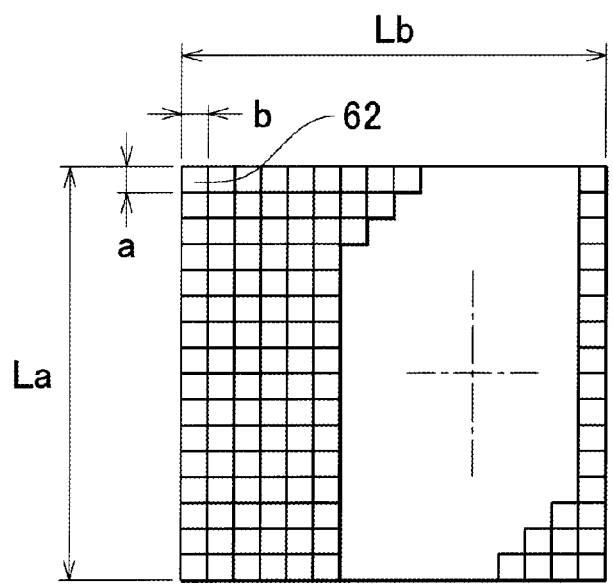
FIG. 17A is a schematic view of an example of the pixel layout of a two-dimensional X-ray detector.
Figure 17B:
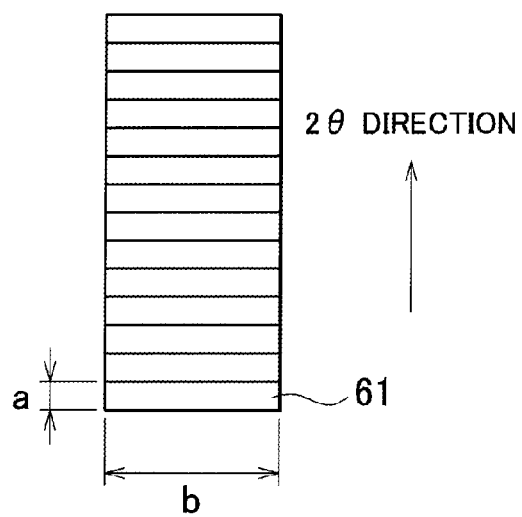
FIG. 17B is a schematic view of an example of the pixel layout of a one-dimensional X-ray detector.

For example, the X-ray detector 11 of FIG. 1 is not limited to being a one-dimensional X-ray detector, but may also be a zero-dimensional X-ray detector. Although a dedicated one-dimensional X-ray detector such as that shown in FIG. 17B is used as the one-dimensional X-ray detector in the embodiment described above, it is also possible to use the necessary pixels 62 of a two-dimensional X-ray detector such as that shown in FIG. 17A as a one-dimensional X-ray detector instead.

EXPLANATION OF SYMBOLS

1. X-ray analyzer, 2. sample stage, 3. incident-side arm, 4. receiving-side arm, 7. X-ray tube, 8. incident-side slit, 11. one-dimensional X-ray detector, 12. θs-rotation drive device, 13. control device, 14. θd-rotation drive device, 17. slit opening/closing drive device, 18. X-ray intensity-calculating circuit, 19. Zs-movement device, 20. center slit, 21. optical axis adjustment jig, 22. shielding strip, 22a. X-ray-incident side of the shielding strip, 51. fixed-sample X-ray analyzer, 52. sample stage, 53. zero-dimensional X-ray detector, 54. incident-side slit, 55. incident-side arm, 56. receiving-side slit, 57. receiving-side arm, 58. optical axis adjustment jig, 59a,59b. reference surfaces, 61,62. pixels, D0. full width at half maximum intensity (FWHM), F. X-ray focus (X-ray source), I0. line of a constant intensity, P1. X-ray profile, P2. corrected X-ray profile, P3. Profile of −0.5 mm, P4. Profile of −0.2 mm, P5. corrected X-ray profile, PP3,PP4. peak, Q1. first position for Zs-axis, Q2. second position for Zs-axis, R0. centerline of X-rays (X-ray optical axis), R1. centerline of diffracted X-rays, S. sample, X0. sample axis,

The invention claimed is:

1. An optical axis adjustment device for an X-ray analyzer comprising:
    an incident-side arm that rotates around a sample axis passing through a sample position constituting a position at which a sample is placed;
    a receiving-side arm that rotates around the sample axis and extends toward a side opposite the incident-side arm;
    an X-ray source provided on the incident-side arm;
    an incident-side slit provided on the incident-side arm between the sample position and the X-ray source;
    an X-ray detector provided on the receiving-side arm;
    a shielding strip disposed at a position blocking X-rays received by the X-ray detector from the X-ray source, the shielding strip extending only in a receiving direction from the sample axis, and
    shielding strip-moving means for rotating the shielding strip around the sample axis relative to an optical axis of the X-rays reaching the X-ray detector from the X-ray source to two different angle positions;
    wherein an amount of deviation in parallelism of the surface of the sample with respect to the optical axis of the X-rays is found on the basis of X-ray intensity values found by the X-ray detector for each of the two angle positions.

2. The X-ray analyzer optical axis adjustment device according to claim 1, wherein an X-ray-incident side of the shielding strip is aligned with the sample axis.

3. The X-ray analyzer optical axis adjustment device according to claim 2, wherein the two angles for the shielding strip are set to a positive-side angle and a negative-side angle so as to cancel out information for the thickness of the shielding strip and obtain only angle information for the shielding strip.

4. The X-ray analyzer optical axis adjustment device according to claim 3, wherein the length of the shielding strip in a direction along the sample axis is greater than the width of the incident X-ray beam in a direction along the sample axis.

5. The X-ray analyzer optical axis adjustment device according to claim 4, wherein the X-ray detector is a one-dimensional X-ray detector possessing X-ray intensity positional resolution, that is the ability to detect X-ray intensity in predetermined regions on a straight line, and the straight line along which the positional resolution is applied extends in a direction along the X-ray angle of diffraction.

6. The X-ray analyzer optical axis adjustment device according to claim 1, wherein the length of the shielding strip in a direction along the sample axis is greater than the width of the incident X-ray beam in a direction along the sample axis.

7. The X-ray analyzer optical axis adjustment device according to claim 1, wherein the X-ray detector is a one-dimensional X-ray detector possessing X-ray intensity positional resolution, that is the ability to detect X-ray intensity in predetermined regions on a straight line, and the straight line along which the positional resolution is applied extends in a direction along the X-ray angle of diffraction.

* * * * *